(12) United States Patent
Duffy et al.

(10) Patent No.: US 10,925,727 B2
(45) Date of Patent: Feb. 23, 2021

(54) MEDICAL DEVICE DELIVERY SYSTEM AND METHODS OF DELIVERING A MEDICAL DEVICE

(71) Applicant: Medtronic CV Luxembourg S.a.r.l., Luxembourg (LU)

(72) Inventors: Niall Duffy, Ballybrit (IE); John Gallagher, Ballybrit (IE); Gerry McCaffrey, Ballybrit (IE); Noam Miller, Netanya (IL); Glenn Stante, Santa Rosa, CA (US)

(73) Assignee: MEDTRONIC CV LUXEMBOURG S.A.R.L., Luxembourg (LU)

( * ) Notice: Subject to any disclaimer, the term of this patent is extended or adjusted under 35 U.S.C. 154(b) by 267 days.

(21) Appl. No.: 15/863,944

(22) Filed: Jan. 7, 2018

(65) Prior Publication Data
US 2018/0125655 A1 May 10, 2018

Related U.S. Application Data

(62) Division of application No. 13/681,529, filed on Nov. 20, 2012, now abandoned.

(51) Int. Cl.
*A61F 2/24* (2006.01)
*A61M 29/00* (2006.01)
*A61F 2/95* (2013.01)

(52) U.S. Cl.
CPC .......... *A61F 2/2436* (2013.01); *A61F 2/9522* (2020.05); *A61M 29/00* (2013.01)

(58) Field of Classification Search
CPC .................. A61M 29/00; A61M 29/02; A61M 2029/025; A61M 25/0194; A61M 25/0119; A61M 25/09; A61M 25/0067; A61M 25/0069; A61M 25/0068; A61M 25/04; A61F 2/2436; A61F 2/962; A61F 2/966; A61F 2/97; A61F 2/2427; A61F 2/95; A61F 2/9522
See application file for complete search history.

(56) References Cited

U.S. PATENT DOCUMENTS

| 3,908,637 | A | | 9/1975 | Doroshow |
| 4,123,091 | A | | 10/1978 | Cosentino et al. |
| 4,573,981 | A | | 3/1986 | McFarlane |
| 5,049,138 | A | | 9/1991 | Chevalier et al. |
| 5,071,413 | A | | 12/1991 | Utterberg |
| 5,267,960 | A | * | 12/1993 | Hayman .............. A61N 5/1027 600/3 |

(Continued)

FOREIGN PATENT DOCUMENTS

WO 2009/137359 A1 11/2009

*Primary Examiner* — Robert A Lynch

(57) ABSTRACT

A medical device delivery system can include a dilator including a tip having a taper in a distal direction, a coupler, and a flap that radially protrudes from the tip. The flap can be configured to bend against a body lumen to cover at least a portion of the delivery system when the dilator is tracked through the body lumen. A medical device delivery system can include a dilator including a tip having a lumen and a coupler having a lumen. The coupler can be configured to securely connect to the tip such that the lumen of the tip is aligned with the lumen of the coupler to allow a guide wire to pass therethrough. Methods for loading a medical device into a delivery catheter are also disclosed.

21 Claims, 11 Drawing Sheets

(56) References Cited

U.S. PATENT DOCUMENTS

| | | | |
|---|---|---|---|
| 5,401,257 A | 3/1995 | Chevalier, Jr. et al. | |
| 5,445,646 A * | 8/1995 | Euteneuer | A61F 2/95 604/103.02 |
| 5,509,900 A * | 4/1996 | Kirkman | A61M 25/0082 604/104 |
| 5,800,443 A * | 9/1998 | Shah | A61B 90/36 606/108 |
| 5,827,324 A * | 10/1998 | Cassell | A61B 17/221 606/200 |
| 5,833,605 A * | 11/1998 | Shah | A61B 5/1076 600/393 |
| 5,931,776 A | 8/1999 | Dotolo | |
| 6,332,877 B1 | 12/2001 | Michels | |
| 6,663,652 B2 * | 12/2003 | Daniel | A61B 17/22031 606/200 |
| 6,790,221 B2 | 9/2004 | Monroe et al. | |
| 7,147,622 B2 | 12/2006 | Gutierrez | |
| 7,235,095 B2 | 6/2007 | Haverkost et al. | |
| 7,887,573 B2 | 2/2011 | Haverkost et al. | |
| 8,048,058 B2 | 11/2011 | Fulford | |
| 2002/0099407 A1 * | 7/2002 | Becker | A61F 2/013 606/200 |
| 2003/0028153 A1 * | 2/2003 | Brennan | A61M 25/0662 604/263 |
| 2003/0176909 A1 * | 9/2003 | Kusleika | A61F 2/95 623/1.11 |
| 2003/0212410 A1 * | 11/2003 | Stenzel | A61F 2/95 606/108 |
| 2004/0024441 A1 * | 2/2004 | Bertolino | A61F 2/95 623/1.12 |
| 2004/0267281 A1 | 12/2004 | Harari et al. | |
| 2005/0101968 A1 * | 5/2005 | Dadourian | A61F 2/95 606/108 |
| 2005/0228475 A1 | 10/2005 | Keeble et al. | |
| 2007/0260158 A1 * | 11/2007 | McLaren | A61M 25/09 600/585 |
| 2008/0228146 A1 * | 9/2008 | Shaked | A61M 25/04 604/180 |
| 2009/0093876 A1 | 4/2009 | Nitzan et al. | |
| 2009/0112062 A1 | 4/2009 | Bakos | |
| 2009/0125036 A1 * | 5/2009 | Bleich | A61B 17/1671 606/110 |
| 2009/0216221 A1 * | 8/2009 | Davis | A61B 18/082 606/33 |
| 2010/0049313 A1 | 2/2010 | Alon et al. | |
| 2010/0057184 A1 * | 3/2010 | Randolph | A61F 2/962 623/1.12 |
| 2010/0125322 A1 | 5/2010 | Fitzgerald et al. | |
| 2010/0249491 A1 * | 9/2010 | Farnan | A61M 1/3653 600/16 |
| 2010/0318172 A1 * | 12/2010 | Schaefer | A61M 25/09 623/1.11 |
| 2011/0184509 A1 * | 7/2011 | Von Oepen | A61F 2/95 623/1.23 |
| 2012/0149978 A1 * | 6/2012 | Olivera | A61B 5/1076 600/104 |
| 2012/0271411 A1 * | 10/2012 | Duhay | A61F 2/2418 623/2.11 |
| 2013/0131775 A1 | 5/2013 | Hadley et al. | |
| 2013/0268051 A1 * | 10/2013 | Atlani | A61F 2/958 623/1.11 |

\* cited by examiner

US 10,925,727 B2

MEDICAL DEVICE DELIVERY SYSTEM AND METHODS OF DELIVERING A MEDICAL DEVICE

CROSS-REFERENCE TO RELATED APPLICATIONS

This application is a division of U.S. patent application Ser. No. 13/681,529 filed Nov. 20, 2012, the contents of which are incorporated by reference herein in their entirety.

BACKGROUND

Field

Certain embodiments of the present invention are related to medical device delivery systems and methods of delivering a medical device.

Background Art

Existing medical device delivery systems, such as those for use in percutaneous medical procedures, can allow a medical device to be delivered through a patient's vascular to a delivery site where it can be implanted within a patient. In some procedures a medical device in the form of a valve prosthesis can be compacted and loaded onto a delivery device for advancement through a patient's vasculature in a transfemoral, transapical, and/or transatrial procedure. There is a continuous need for improved delivery systems for use in percutaneous and other delivery techniques.

BRIEF SUMMARY

In some embodiments, a medical device delivery system can include a dilator including a tip having a taper in a distal direction, a coupler, and a flap that radially protrudes from the tip. The flap can be configured to bend against a body lumen to cover at least a portion of the delivery system when the dilator is tracked through the body lumen.

In some embodiments, a medical device delivery system can include a dilator including a tip having a lumen and a coupler having a lumen. The coupler can be configured to securely connect to the tip such that the lumen of the tip is aligned with the lumen of the coupler to allow a guide wire to pass therethrough. Methods for loading a medical device into a delivery catheter are also disclosed.

In some embodiments, a method of loading a medical device into a delivery catheter can include securing a coupler to a delivery catheter shaft, the shaft having a lumen for receiving the medical device, crimping the medical device to a diameter permitting the medical device to be loaded into the shaft lumen, loading the medical device into the shaft lumen, and securing a dilator tip to the coupler after the medical device is loaded into the shaft lumen.

BRIEF DESCRIPTION OF THE DRAWINGS/FIGURES

The accompanying figures, which are incorporated herein, form part of the specification and illustrate embodiments of percutaneous medical procedure systems and related methods. Together with the description, the figures further serve to explain the principles of and to enable a person skilled in the relevant art(s) to make, use, and implant the valve prosthesis described herein.

Figure 2:
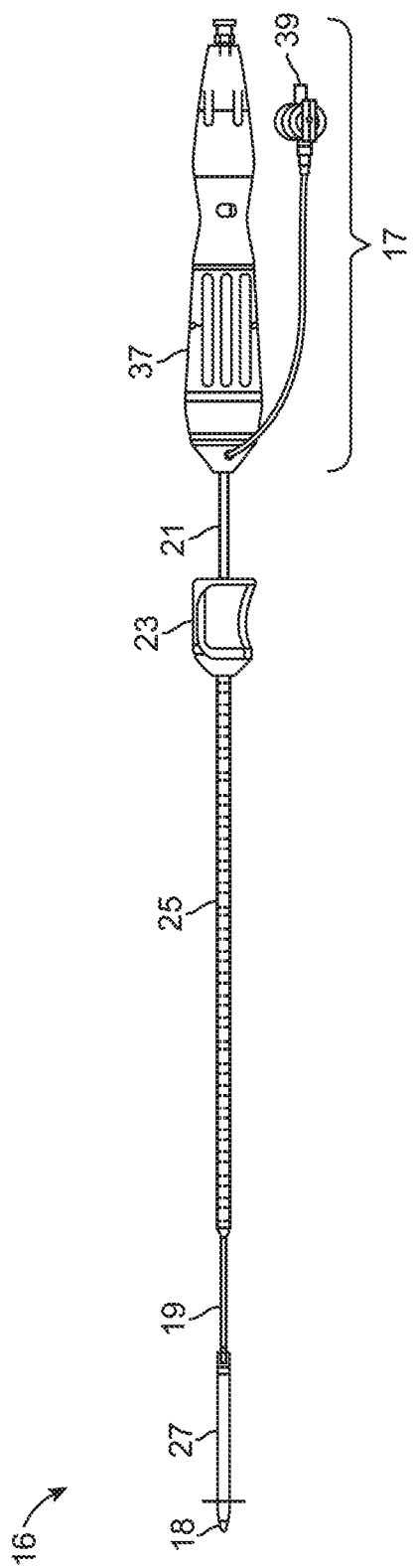
FIG. 2 illustrates a delivery system in accordance with one embodiment.

FIGS. 3a-c and 4a-c illustrate the delivery system of FIG. 2 in various states.

Figure 5:
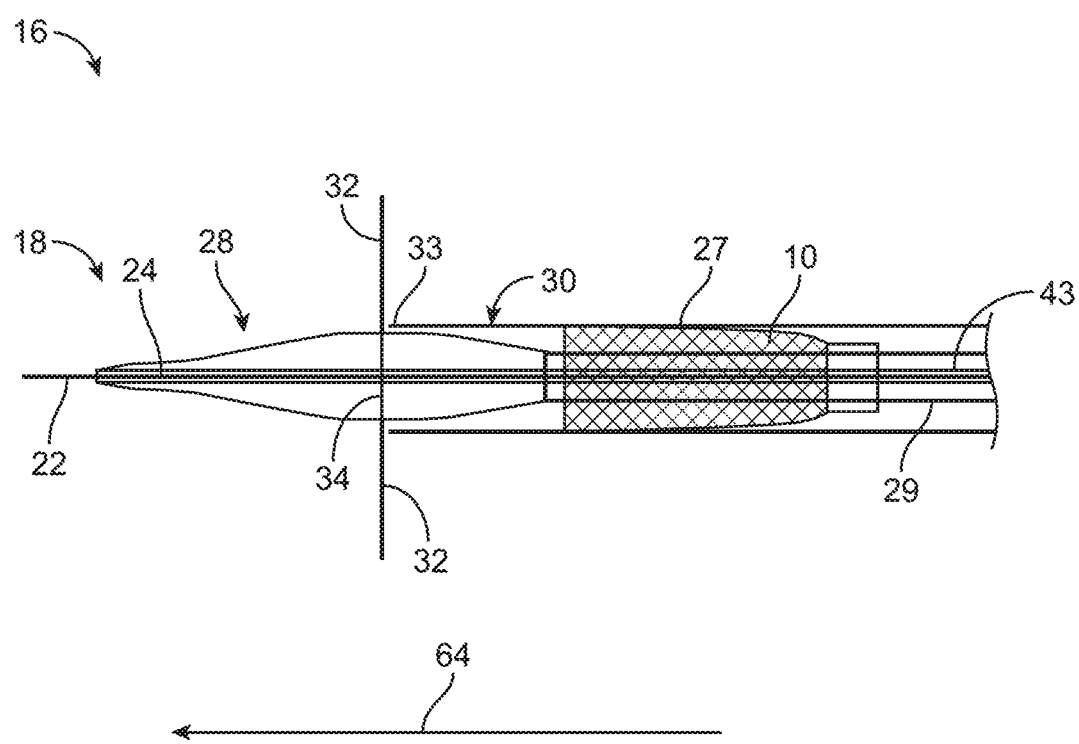

FIG. 5 illustrates a cross-sectional view of a portion of the delivery system of FIG. 2.

Figure 6:
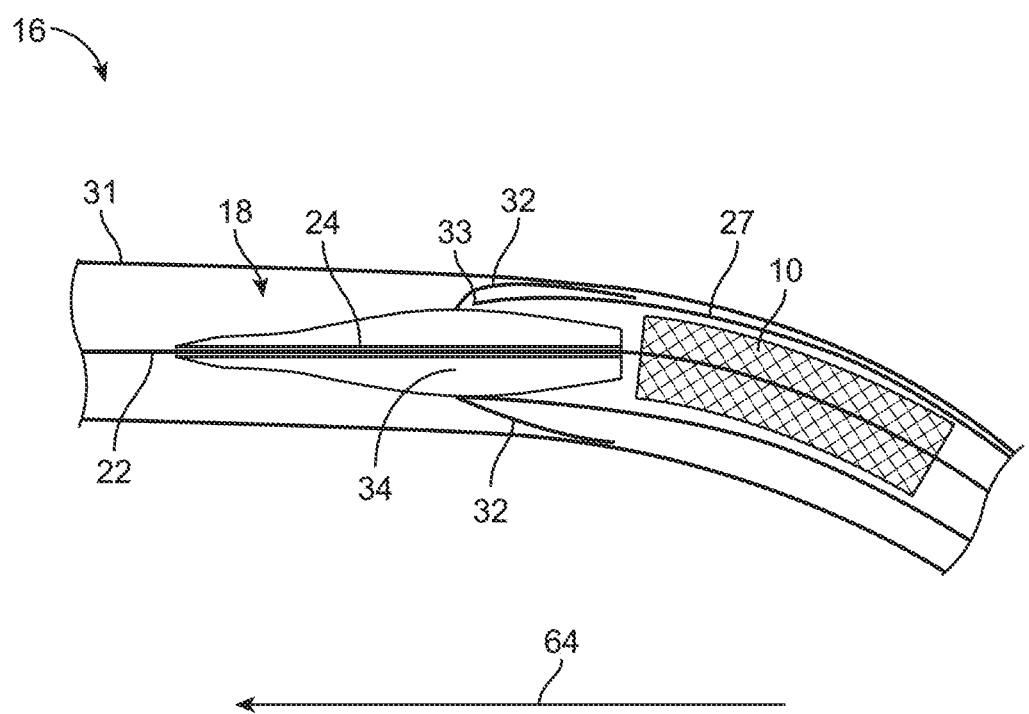

FIG. 6 illustrates a cross-sectional view of a portion of the delivery system of FIG. 2 in a body lumen.

Figure 7:
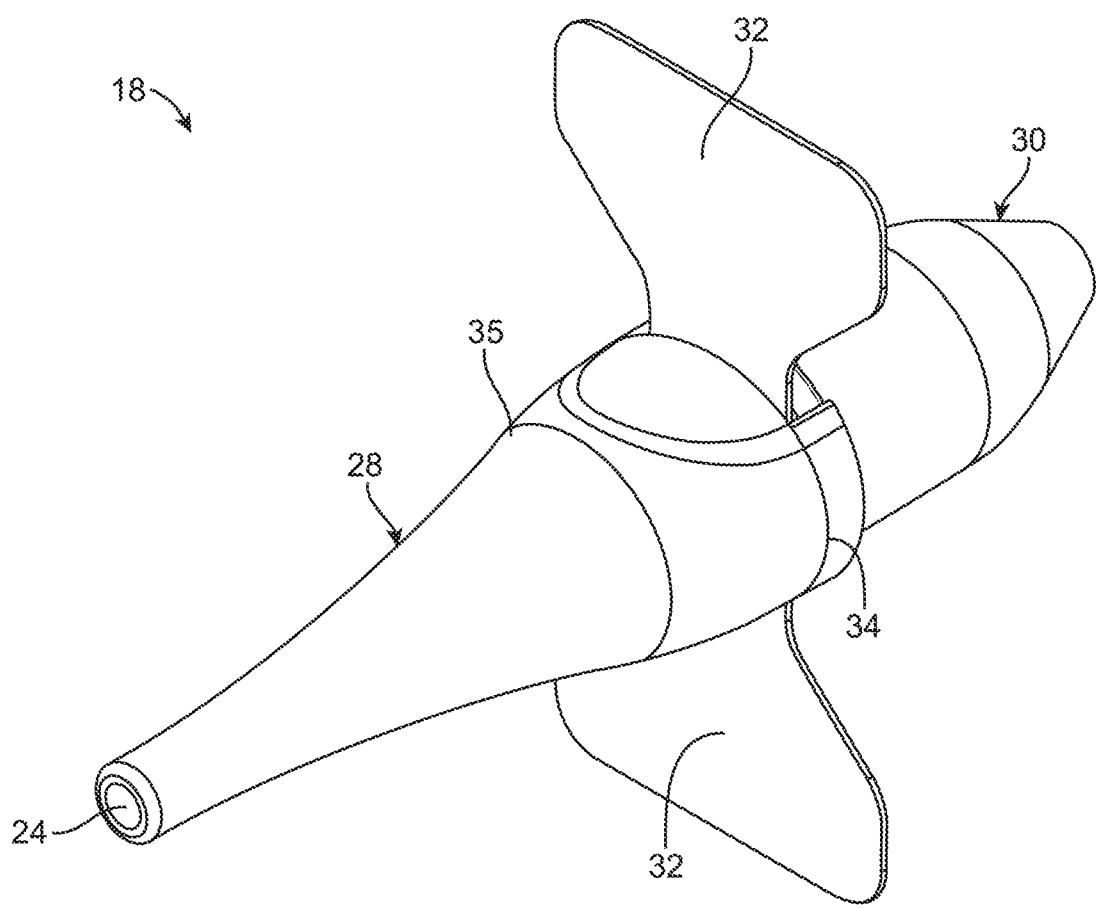

FIG. 7 illustrates a front perspective view of a dilator in accordance with one embodiment.

Figure 8:
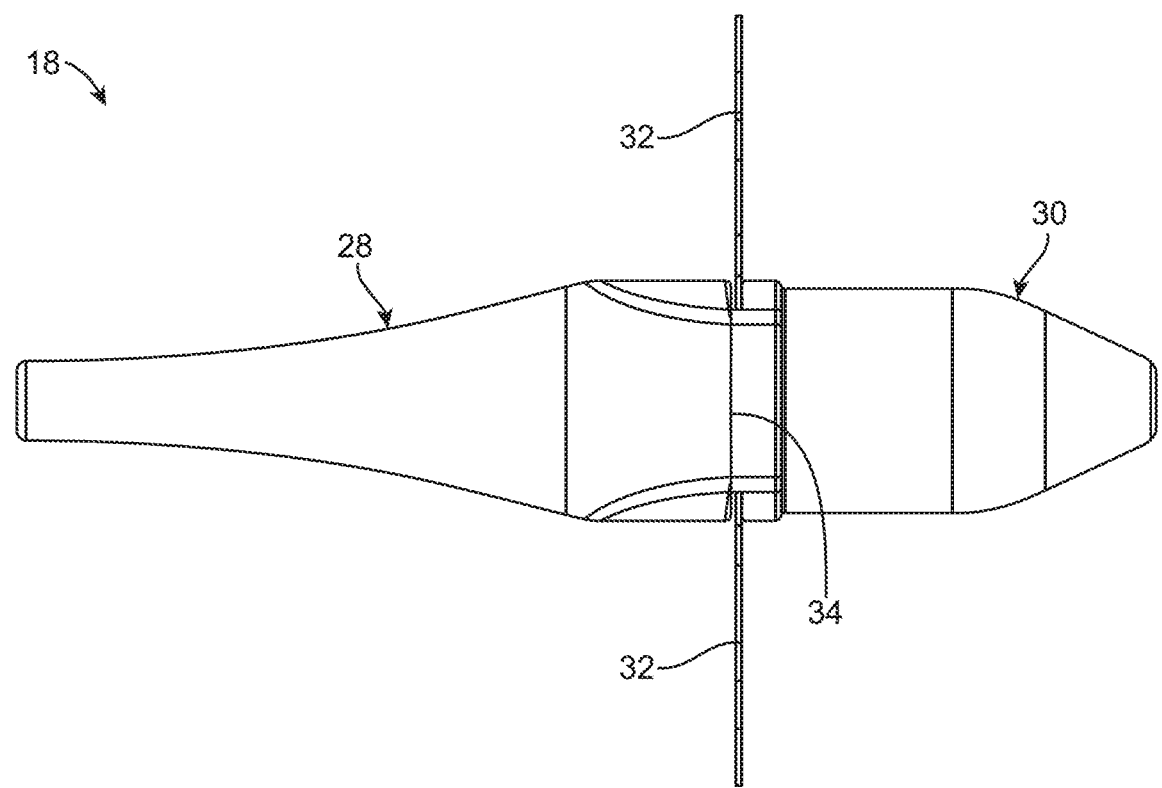

FIG. 8 illustrates a side view of the dilator of FIG. 7.

Figure 9:
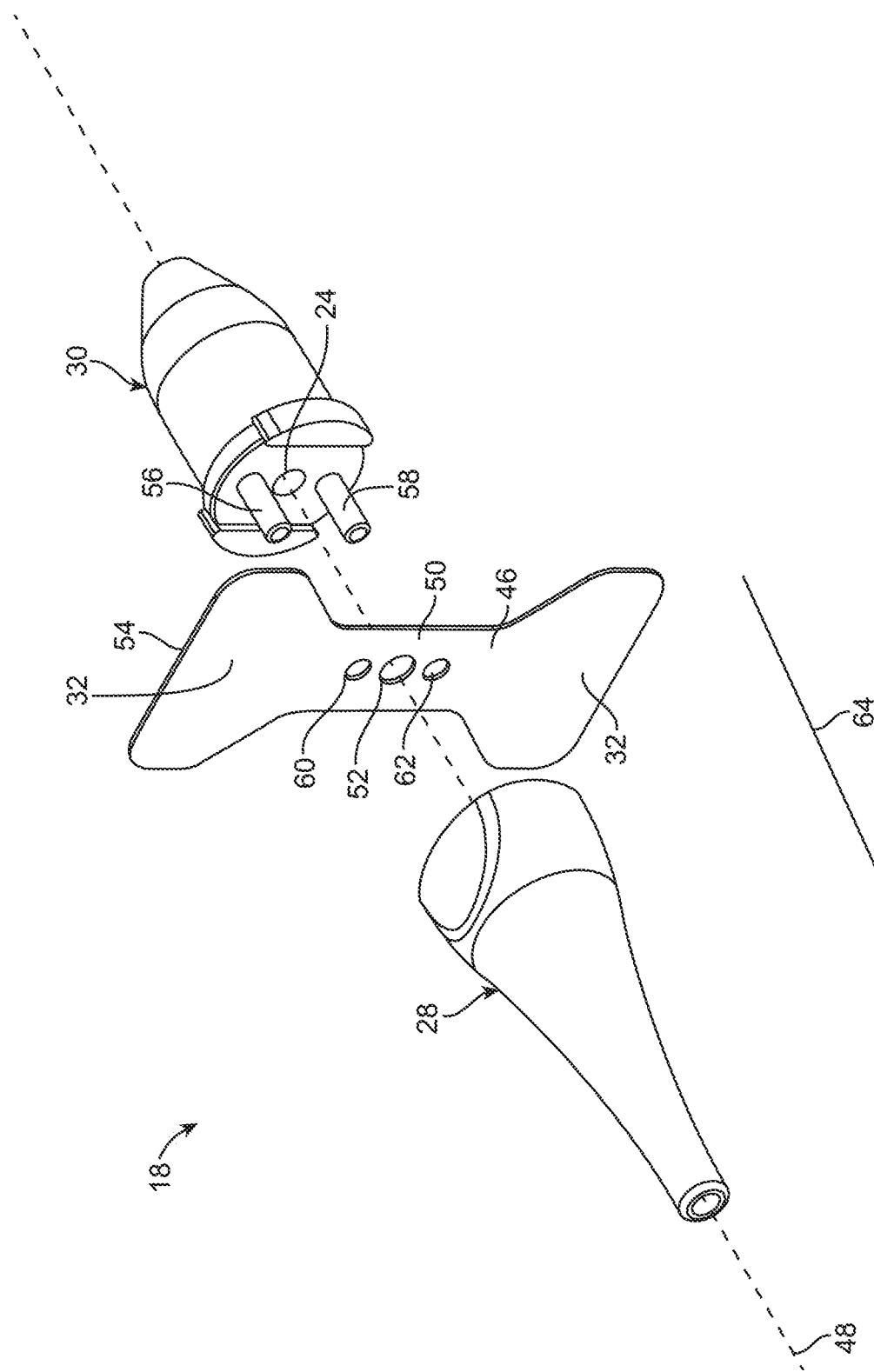

FIG. 9 illustrates an exploded view of the dilator of FIG. 7.

Figure 10:
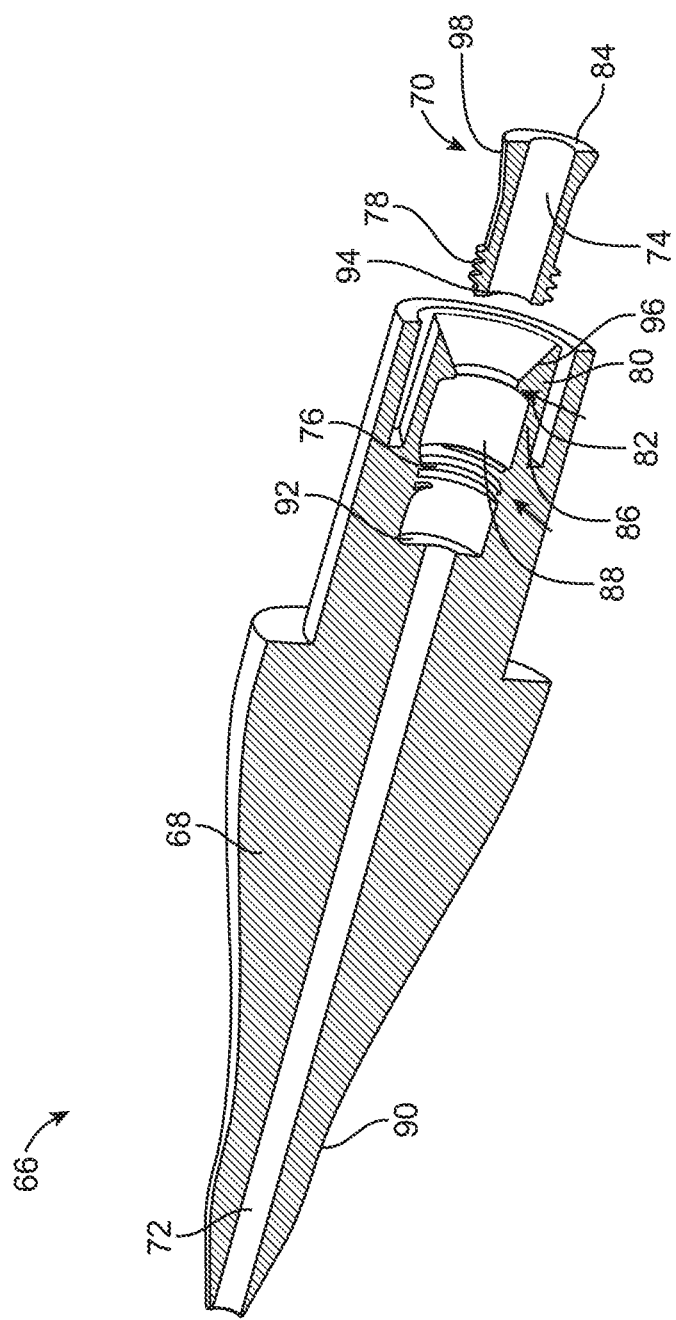

FIG. 10 illustrates a cross-sectional view of a dilator in accordance with one embodiment in a first state.

Figure 11:
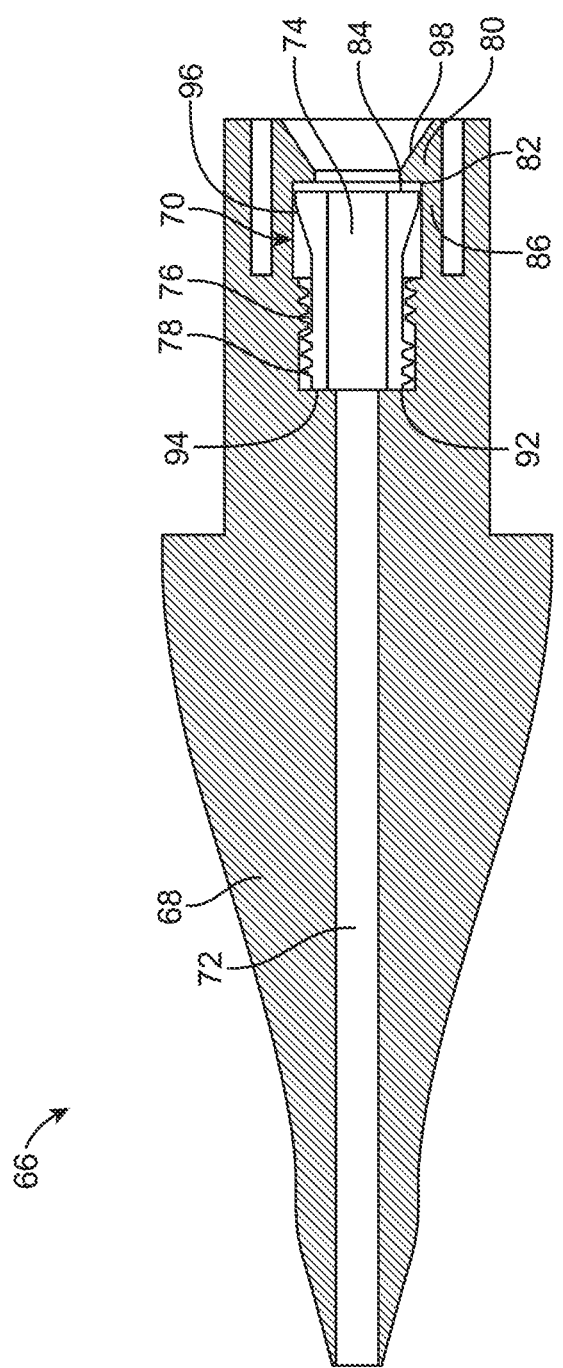

FIG. 11 illustrates a cross-sectional view of the dilator of FIG. 10 in a second state.

DETAILED DESCRIPTION

The following detailed description refers to the accompanying figures which illustrate several embodiments. Other embodiments are possible. Modifications can be made to the embodiments described herein without departing from the spirit and scope of the present invention. Therefore, the following detailed description is not meant to be limiting.

Figure 1:
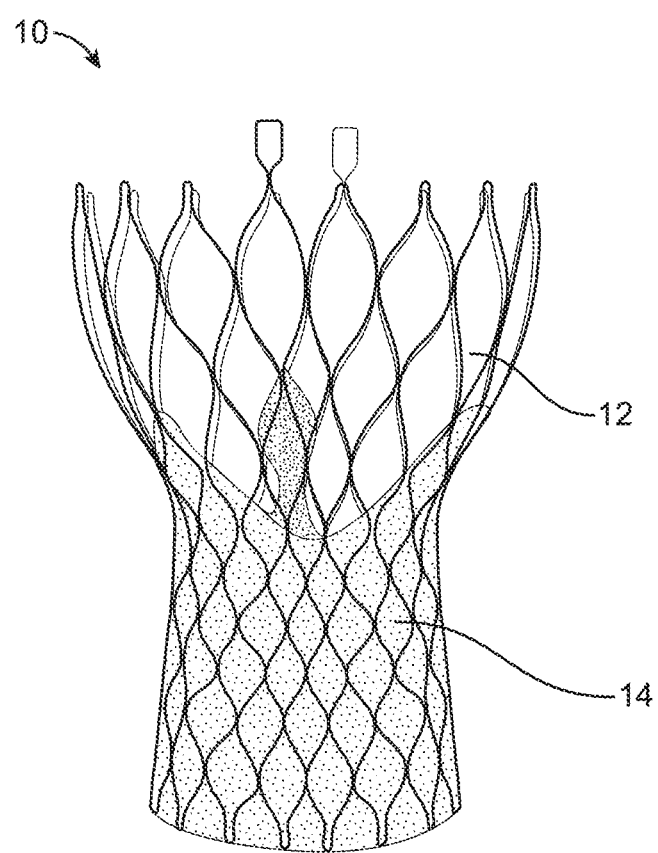
FIG. 1 illustrates a front view of a medical device that can be used in one or more of the systems described herein.

FIG. 1 illustrates a medical device 10 that can be used in one or more of the systems described herein. In some embodiments, medical device 10 can be in the form of a prosthetic heart valve including a frame 12 attached to a valve body 14. In some embodiments, valve body 14 can be formed, for example, from one or more of biocompatible synthetic materials, synthetic polymers, autograft tissue, homograft tissue, xenograft tissue, or one or more other suitable materials. In some embodiments, valve body 14 can be formed, for example, from bovine, porcine, equine, ovine, and/or other suitable animal tissues. In some embodiments, valve body 14 can be formed, for example, from heart valve tissue, pericardium, and/or other suitable tissue. In some embodiments, valve body 14 can comprise one or more valve leaflets, such as for example, a tri-leaflet bovine pericardium valve, a bi-leaflet valve, or another suitable valve.

A suitable medical device 10 is not limited to prosthetic heart valves. In some embodiments, medical device 10 can be a device configured to be transported via a delivery catheter. In some embodiments, medical device 10 can be an expandable device, such as, for example, a percutaneously delivered device configured to be compacted and loaded onto a delivery catheter for advancement through a natural or artificial body lumen, such as for example through a patient's vasculature. In some embodiments, medical device 10 is not expandable. In some embodiments, medical device 10 is not designed to be implanted within the patient's body. In some embodiments, medical device 10 can be an embolic filter. In some embodiments, medical device 10 can be a tool that can be used, for example, to retrieve an item from inside a patient.

FIG. 2 illustrates a delivery system 16 in accordance with one embodiment of the present invention. In some embodiments, system 16 can be used in one or more percutaneous delivery procedures. For example, in some percutaneous procedures, a valve prosthesis can be compacted and loaded onto a delivery device, such as for example a catheter, for advancement through a patient's vasculature. In some embodiments, system 16 can be configured for use in illiofemoral, apical, radial, direct aortic, and subclavian/axillary entry locations. System 16 can be configured to allow access from multiple locations per procedure (e.g. bilateral femoral access). In some embodiments, system 16 can be configured to deliver medical device 10 through an artery or vein, a femoral artery, a femoral vein, a jugular vein, a subclavian artery, an axillary artery, an aorta, an atrium, and/or a ventricle. System 16 can be configured to deliver medical device 10 via a transfemoral, transapical, transseptal, transatrial, transventrical, or transaortic procedure. In some embodiments, one or more components or portion of components of system 16 can be configured to flex to facilitate the traversal of system 16 through a body lumen during a delivery procedure. In some embodiments, one or more components of system 16 or portions thereof can include a curved outer surface and/or shape to facilitate movement through a curved body lumen.

As described above, in some embodiments, system 16 can be configured for use in a transfemoral delivery procedure. In one example of such a procedure, a delivery device including a prosthetic heart valve can be advanced in a retrograde manner through a patient's femoral artery and into the patient's descending aorta. A catheter can then be advanced under fluoroscopic guidance over the simulated aortic arch, through the ascending aorta, into the left ventricle, and mid-way across the defective aortic valve. Once positioning of the catheter is confirmed, the valve prosthesis can be deployed within the valve annulus. The valve prosthesis can then expand against the simulated annulus. In some embodiments, as the valve prosthesis is expanded, it can trap leaflets against the annulus, which can retain the native valve in a permanently open state.

As described above, in some embodiments, system 16 can be configured for use in a transapical delivery procedure. In one example of such a procedure, a trocar or overtube can be inserted into a patient's left ventricle through an incision created in the apex of the patient's heart. A dilator can be used to aid in the insertion of the trocar. In this approach, the native valve (for example, the mitral valve) can be approached downstream relative to blood flow. The trocar can be retracted sufficiently to release the self-expanding valve prosthesis. The dilator can be presented between the leaflets. The trocar can be rotated and adjusted to align the valve prosthesis in a desired alignment. The dilator can be advanced into the left atrium to begin disengaging the proximal section of the valve prosthesis from the dilator.

In some embodiments, system 16 can be configured for use in a transatrial delivery procedure. In one example of such a procedure, a dilator and trocar can be inserted through an incision made in the wall of the left atrium of the heart. The dilator and trocar can then be advanced through the native valve and into the left ventricle of the heart. The dilator can then be withdrawn from the trocar. A guide wire can be advanced through the trocar to the point where the valve prosthesis comes to the end of the trocar. The valve prosthesis can be advanced sufficiently to release a self-expanding valve prosthesis from the trocar. The trocar can be rotated and adjusted to align the valve prosthesis in a desired alignment. The trocar can be withdrawn completely from the heart such that the valve prosthesis self-expands into position and can assume the function of the native valve.

The few example procedures described above are not intended to be exhaustive. It is understood that not every act need be performed and additional acts can be included as would be apparent to one of ordinary skill in the art. In addition, the acts can be reordered as desired. Other medical devices and delivery techniques can be used with any of the parts described herein. It is further understood that the above delivery routes are merely exemplary and that other suitable delivery routes can be employed. The terms "delivery" and "delivery system" as used herein is intended to refer broadly to positioning a medical device at a desired location and related systems. Such terms do not necessitate a system that actually deposits a medical device at a site, such as for example a device that can be used to implant a prosthetic heart valve. The term "delivery system" can cover, for example, a system that temporarily positions a medical device at a desired location. For example, the delivery system can be used to position an embolic filter at a desired location within a patient's vascular for a period of time before removing the embolic filter.

The delivery system 16 of FIG. 2 can include a handle 17, one or more retractable sheaths 19 and 21, a hub 23, an introducer 25, a capsule 27, and a dilator 18. In some embodiments, dilator 18 can be configured to dilate a tube, cavity, and/or opening in the body to facilitate introduction of system 16 for a delivery procedure. In some embodiments, dilator 18 can be configured to facilitate removal of system 16 following delivery of medical device 10.

In some embodiments, dilator 18 can be connected to handle 17 via one or more inner shafts (see, for example, shaft 29 described below with respect to FIG. 5). In some embodiments, one or more of handle 17, retractable sheaths 19 and 21, hub 23, introducer 25, and capsule 27 can be slidably disposed over one or more of the inner shafts. In some embodiments, capsule 27 can be configured to releasably engage with dilator 18. In some embodiments, a distal edge 33 of capsule 27 can abut a proximal end of dilator 18.

In some embodiments, capsule 27 can be configured to house medical device 10 for delivery via system 16. Capsule 27 can include a lumen (shown for example in FIG. 5) that is configured to receive the entirety of medical device 10 or a portion thereof. In some embodiments, capsule 27 can be in the form of a tube or another suitable shape. In some embodiments, capsule 27 can be in the form of a sheath. In some embodiments, a portion of capsule 27 can be tapered. For example, in some embodiments, one or both of a proximal and distal end portions of capsule 27 can be tapered.

In some embodiments, capsule 27 can be configured to move relative to medical device 10 to partially or fully release medical device 10 for delivery by system 16. In some embodiments, system 16 is configured to move capsule 27 relative to medical device 10 by moving capsule 27 from a first position to a second position while medical device 10 is relatively stationary. For example, in some embodiments, capsule 27 can be configured to move in a proximal direction relative to medical device 10 (towards handle 17) to partially or fully expose medical device 10 to allow for delivery medical device 10. In some embodiments, system 16 is configured to move capsule 27 relative to medical device 10 by moving medical device 10 from a first position to a second position while capsule 27 is relatively stationary. For example. In some embodiments, medical device 10 can be pushed relative to capsule 27 in a distal direction to partially or fully expose medical device 10 for delivery in system 16.

In some embodiments, movement of capsule 27 can be automatically or manually actuated. In some embodiments, handle 17 can include a control knob 37 configured to retract capsule 27. In some embodiments, movement of capsule 27 can be controlled by a user, such as by rotating control knob 37 on handle 17 or via another suitable actuator. In some embodiments, one or more portions of system 16 can include a flushing port 39, which in some embodiments can be configured to maintain hemostasis during a medical procedure. Flushing port 39 can be connected to handle 17, or another suitable portion of system 16. In some embodiments, one or more portions of system 16, such as for example an exterior of capsule 27 can be coated with a biocompatible lubricant.

In some embodiments, hub 23 can include an integrated hemostasis control feature. Hub 23 can be connected to introducer 25 and can be configured to move introducer 25 by sliding hub 23 distally towards dilator 18. In some embodiments, hub 23 can include a feature, such as for example a spring-loaded button, that can be configured to avoid accidental movement of hub 23 during a procedure.

In some embodiments, introducer 25 can be in the form of a flexible sheath. In some embodiments, introducer 25 can be used to push capsule 27 against dilator 18 after medical device 10 has been delivered. In some embodiments, introducer 25 can be configured to cover the exposed edges of capsule 27, which in some embodiments can facilitate retraction through the deployed prosthesis. In some embodiments, once medical device 10 is released and expands against a body lumen, a user can slide hub 23 in a distal direction. System 16 can be configured such that distal movement of hub 23 will move introducer 25 in a distal direction. In some embodiments, system 16 is configured such that distal movement of introducer 25 will thereby slide capsule 27 to engage a proximal end of dilator 18.

Figure 3A:
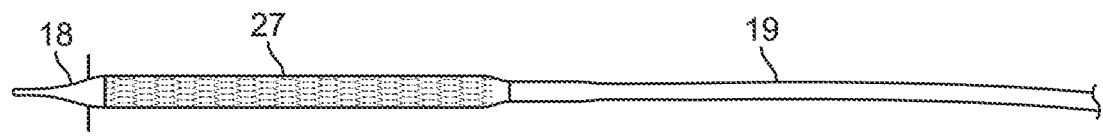
Figure 3B:
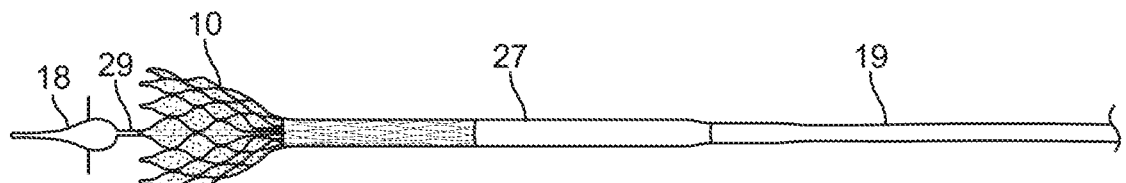
Figure 3C:
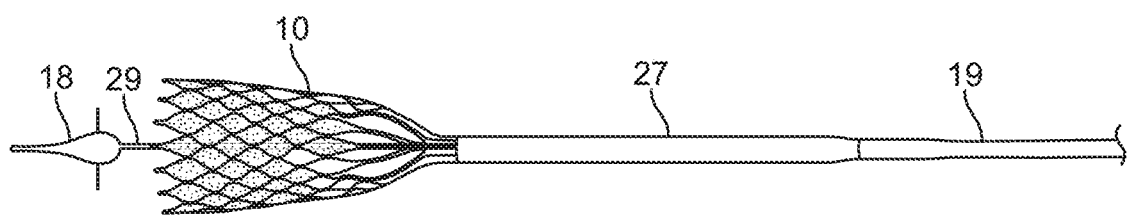
Figure 4A:
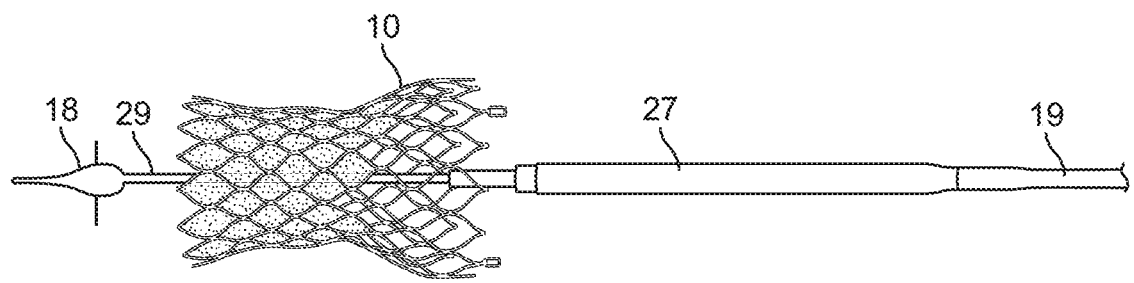
Figure 4B:
Figure 4C:
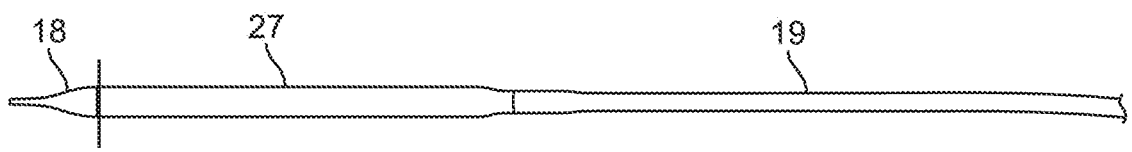

As described above, in some embodiments, system 16 can be configured for use in a percutaneous delivery procedure including a medical device that is compacted and loaded into system 16 for advancement through a patient's vasculature. FIGS. 3a-c and 4a-c illustrate various stages of one example of a delivery procedure. In particular, FIG. 3a illustrates delivery system 16 with medical device 10 fully housed within capsule 27. FIG. 3b illustrates sheath 19 and capsule 27 partially retracted to expose a portion of medical device 10. FIG. 3c illustrates sheath 19 and capsule 27 further retracted to further expose medical device 10. FIG. 4a illustrates sheath 19 and capsule 27 completely retracted to fully expose medical device 10. FIGS. 4b and 4c illustrate stages of capsule 27 being returned to dilator 18 after delivery of medical device 10. In particular, FIG. 4b illustrates delivery system 16 with capsule 27 partially returned to dilator 18. FIG. 4c illustrates delivery system 16 with capsule 27 engaged with dilator 18 with system 16 ready to be retracted from the body lumen. In some embodiments, capsule 27 does not engage with dilator 18 before system 16 is retracted from the body lumen.

FIG. 5 illustrates a cross-sectional view of a medical device delivery system 16 in accordance with one embodiment. As described above, delivery system 16 can include medical device 10, dilator 18, and capsule 27. System 16 can further include a shaft 29 and a guide wire 22. Dilator 18 and shaft 29 can include respective lumens 24 and 43 formed therein for receiving guide wire 22 such that dilator 18 and shaft 29 are slidably disposed relative to guide wire 22. In some embodiments, medical device 10 can be crimped around shaft 29.

In some conditions, an edge 33 of capsule 27 can align with dilator 18 such that it allows for a substantially continuous surface with dilator 18. However, in other conditions, such as while traversing a body lumen, a gap can be created between dilator 18 and edge 33 of capsule 27. In some embodiments, such a gap can be formed as a result of capsule 27 "fish mouthing", which can occur when a portion of edge 33 is bent in a shape resembling an open fish mouth. In some cases, a gap between dilator 18 and capsule 27 can undesirably scrape an inside of a body lumen. In some cases, a gap between dilator 18 and capsule 27 can cause damage to one or more of capsule 27, dilator 18, medical device 10, or another component of system 16.

In order to avoid complications relating to fish mouthing, or for other advantages, delivery system 16 can be configured to cover a gap formed between capsule 27 and dilator 18 or between other components of system 16. For example, in some embodiments, dilator 18 can include flaps 32 that are configured to cover edge 33 of capsule 27 as system 16 traverses through a body lumen. In some embodiments, flaps 32 can be configured to prevent catching or snagging of the system during implantation or removal of the medical device. For example, in some embodiments, a proximal end of dilator 18 can cover an opening formed by a lumen of capsule 27. In some embodiments, flaps 32 can flex down over a portion of dilator 18 to keep a smooth transition between dilator 18 and capsule 27. In some embodiments, flaps 32 can be configured so that when medical device 10 traverses through a body lumen, one of flaps 32 can be on the outside curvature of medical device 10.

In some embodiments, flaps 32 can reduce or eliminate certain effects when recrossing a native valve, such as a native aortic valve, after resheathing. For example, when some dilators recross a native valve, a distal edge of the dilator or another component can flare out. In some cases, the flared dilator can make it difficult for a physician to cross through a native valve. In some embodiments, flaps 32 can flex down over a portion of dilator 18. In some embodiments, this can provide a smooth transition between dilator 18 and capsule 27, which in some cases can facilitate tracking through a native valve.

In some embodiments, dilator 18 can be assembled such that flaps 32 protrude from dilator 18 at an angle of approximately 90 degrees from axial direction 64. In some embodiments, flaps 32 protrude from dilator 18 at an angle greater than or less than 90 degrees, such as for example approximately 30 degrees, approximately 45 degrees, approximately 120 degrees, or approximately 150 degrees. In some embodiments, one of flaps 32 can protrude at a first angle, such as for example, approximately 90 degrees, and another of flaps 32 can protrude at a second and different angle, such as for example, approximately 30 degrees. In some embodiments, flaps 32 can be made of a thin film of polymer. In some embodiments, flaps 32 can be configured so that they are flexible enough to bend towards first portion 28 and/or second portion 30 of dilator 18 when system 16 is tracked through a body lumen. In some embodiments, flaps 32 can be stiff enough so that flaps 32 straighten back out to be perpendicular to axial direction 64 when flaps 32 are no longer pressed towards first portion 28 or second portion 30.

In some embodiments, flaps 32 are configured to bend so that flaps 32 are substantially parallel to capsule 27. As shown for example in FIG. 9, flaps 32 can be configured to bend towards and over capsule 27 when delivery system 16 is moved relative to a body lumen in a first direction, such as axial direction 64. In some embodiments, this direction can correspond to a direction that dilator 18 moves when medical device 10 is being delivered to a delivery site.

In some embodiments, flaps 32 can additionally be configured to bend towards first portion 28 when delivery system 16 is moved in a direction opposite to the first direction. In some embodiments, the direction opposite to the first direction can correspond to a direction in which dilator 18 moves when delivery system 16 is being retracted from a patient. In some embodiments, an ability of flaps 32 to bend towards first portion 28 can facilitate removing dilator 18 from a body lumen. In some embodiments, flaps 32 can bend towards second portion 30 when dilator 18 is moved towards a delivery site and then be inverted to bend towards first portion 28 when dilator 18 is being retracted. In some embodiments, flaps 32 are configured to only bend in one direction.

FIG. 6 illustrates a cross-sectional view of delivery system 16 bent within a body lumen 31. As shown therein, as dilator 18 bends relative to capsule 27, flap 32 covers edge 33 of capsule 27.

FIGS. 7-9 illustrate various views of dilator 18 in accordance with one embodiment. In particular, FIG. 7 illustrates a front perspective view of dilator 18, FIG. 8 illustrates a side view of dilator 18, and FIG. 9 illustrates an exploded view of dilator 18. In some embodiments, dilator 18 can include a dilator body 35 having a first portion 28 and second portion 30. Dilator 18 can further include one or more flaps 32. In some embodiments, first portion 28 is a distal portion of dilator 18 and second portion 30 is a proximal portion of dilator 18. In some embodiments, first portion 28 and second portion 30 can be two or more pieces attached together. In some embodiments, first portion 28 and second portion 30 can be a monolithic piece of material. In some embodiments, flaps 32 can be ends of a monolithic piece of material. In some embodiments, first portion 28 and second portion 30 abut at a junction 34. In some embodiments, first portion 28 and second portion 30 can be removably attached. In some embodiments, first portion 28 and/or second portion 30 can include respective tapered outer surfaces. In some embodiments, an outer surface of first portion 28 can be configured to induce dilation in a body lumen or another site in a patient.

In some embodiments, first portion 28 can include a lumen configured to allow guide wire 22 to pass therethrough. In some embodiments, second portion 30 can include a lumen configured to allow guide wire 22 to pass therethrough. In some embodiments, the lumen of first portion 28 and the lumen of second portion 30 can be configured to align to form a single lumen 24 that can allow guide wire 22 to pass through both first portion 28 and second portion 30. In some embodiments, only one of first portion 28 and second portion 30 includes a lumen.

In some embodiments, such as for example the embodiment shown in FIG. 9, flaps 32 can be the ends of a single piece 46 of flap material that protrudes from dilator 18 on either side of axis 48 of dilator 18. In some embodiments, piece 46 can be sandwiched between first portion 28 and second portion 30 of dilator 18. In some embodiments, piece 46 can be hourglass shaped, as shown for example in FIG. 9. In some embodiments, a central portion 50 of piece 46 can be narrower than flaps 32 such that flaps 32 include flared distal ends. In some embodiments, central portion 50 can be equal to or wider than flaps 32. In some embodiments, a narrower portion of piece 46 can facilitate the bending of flaps 32 around first portion 28 and/or second portion 30. In some embodiments, piece 46 can be substantially rectangular, circular, elliptical, or a suitable non-geometric shape. In some embodiments, piece 46 can include an opening 52 that corresponds to lumen 24 of dilator 18.

In embodiments including multiple flaps 32, flaps 32 can be formed from separate pieces of flap material. For example, in some embodiments, a left flap can be attached to a left side of dilator 18 and a right flap can be attached to a right side of dilator 18.

In some embodiments, dilator 18 includes only a single flap 32. In some embodiments, dilator 18 includes more than two flaps. For example, in some embodiments, piece 46 can be X-shaped, with four flaps protruding from an outer surface of dilator 18. In some embodiments, flaps 32 can include an end 54 that can be substantially flat, shown for example in FIG. 9. In some embodiments, end 54 can be rounded, or another desired shape.

As further shown in FIG. 9, in some embodiments, one or both of first portion 28 and second portion 30 can include one or more extensions 56 and 58 which can correspond to one or more openings 60, 62 for securing flaps 32. In some embodiments, first portion 28 and second portion 30 are two pieces that are sandwiched around flaps 32 and bonded together. In some embodiments, first portion 28 and second portion 30 are molded around flaps 32 as one piece. In some embodiments, dilator 18 can include recesses where flaps 32 protrude to ensure that when first portion 28 is inserted through an introducer, flaps 32 can fold down within the recess so that dilator 18 can achieve a desired diameter, such as for example 19 Fr or another suitable diameter.

FIGS. 10-11 illustrate a dilator 66 in accordance with one embodiment. In particular, FIG. 10 illustrates a perspective cross-sectional view of dilator 66 in a first state and FIG. 11 illustrates a side cross-sectional view of dilator 66 in a second state. Dilator 66 can be used, for example, in delivery system 16. In some embodiments, dilator 66 can be used for another delivery system. Dilator 66 can include a tip 68 and a coupler 70. In some embodiments, both tip 68 and coupler 70 include respective lumens 72 and 74 formed therein. In some embodiments, lumens 72 and 74 can be configured to align to allow a guide wire to pass therethrough. In some embodiments, tip 68 includes an arm 86 that can flex to securely receive coupler 70. In some embodiments, tip 68 can include an outer surface 90 that is tapered. In some embodiments, tip 68 includes a cavity 88 configured to receive coupler 70. In some embodiments, cavity 88 can be configured to partially receive coupler 70. In some embodiments, cavity 88 can be configured to receive the entirety of coupler 70.

In FIG. 10, coupler 70 is shown disengaged from tip 68. However, as shown for example in FIG. 11, tip 68 and coupler 70 can be joined together to restrain movement between coupler 70 and dilator 66. For example, in some embodiments, tip 68 and coupler 70 can be joined via threads 76 and 78. In some embodiments, tip 68 and coupler 70 can include a collet 80 having a stepped surface 82 corresponding to an end surface 84 of coupler 70 to prevent removal of coupler 70 from tip 68. In some embodiments, collet 80 can include an angled surface 96 which can be configured to facilitate insertion of coupler 70 into cavity 88 of tip 68. In some embodiments coupler 70 includes an angled surface 98 which can be configured to facilitate insertion of coupler 70 into cavity 88 of tip 68. As shown for example in FIG. 11, coupler 70 can be joined to tip 68 via both threads 76 and collet 80. In some embodiments, coupler 70 can be bonded to tip 68 via adhesives or another suitable bonding technique. In some embodiments, coupler 70 can be attached to tip 68 via a clip. In some embodiments, coupler 70 can be attached to tip 68 via a ratchet-style connection. In some embodiments, coupler 70 can be over-moulded onto a shaft or another piece within system 16. Cavity 88 can include a stepped surface 92 configured to abut an end surface 94 of coupler 70 when coupler 70 can be received within cavity 88. In some embodiments, tip 68 is securely coupled to coupler 70 such that tip 68 cannot fall off or be dislodged during delivery of dilator 66.

In some embodiments, a method of loading a medical device, such as medical device 10 into a delivery catheter can include securing coupler 70 to a delivery catheter shaft, the shaft having a lumen for receiving medical device 10. The method can further include crimping medical device 10 to a diameter that permits medical device 10 to be loaded into the shaft lumen. The method can further include loading medical device 10 into the shaft lumen. The method can further include securing dilator tip 68 to coupler 70 after medical device 10 is loaded into the shaft lumen. In some embodiments, tip 68 is secured to coupler 70 by threading dilator tip 68 onto coupler 70, such as via threads 76 and 78. In some embodiments, tip 68 is secured to coupler 70 via a snap fit between the tip 68 and the coupler 70, such as via arm 86 and collet 80. In some embodiments, coupler 70 is secured to the delivery catheter shaft via a press fit. In some embodiments, coupler 70 is secured to the delivery catheter shaft via adhesive or another suitable fastening means.

As described above, in some embodiments, tip 68 can be configured to attach to coupler 70 after a medical device, such as a valve prosthesis has been inserted into a system. In some embodiments, allowing tip 68 to attach to coupler 70 after a medical device has been loaded can increase the options for insertion of the device into the system. In some embodiments, such a configuration can allow tip 68 to be easily and securely attached to the system after loading of the device. In some embodiments, such a configuration can allow for variation in tip design for varying anatomy.

The choice of materials for the various valve prostheses described herein can be informed by the requirements of mechanical properties, temperature sensitivity, biocompatibility, moldability properties, or other factors apparent to a person having ordinary skill in the art. For example, one more of the parts (or a portion of one of the parts) can be made from suitable plastics, such as a suitable thermoplastic, suitable metals, and/or other suitable materials. One or more components or portions of components can be made of the same or similar material as any other component. One or more components or portions of components can be configured such that they are more flexible than another component or portion of component. In some embodiments, one or more components can include radiopaque materials.

In some embodiments, one or more components can include additional and/or embedded structure configured to provide increased mechanical strength while allowing for increased flexibility. In some embodiments, one or more components, such as for example capsule 27 or introducer 25, can include a metal laser cut tube, a wound coil, braid, or other suitable structure for increasing mechanical strength.

In some embodiments, one or more components can be entirely or partially constructed using a single material or a composite material and/or a multi-layer material. In some embodiments, one or more of the components can include a material with a low coefficient of friction. In some embodiments, such a material can, for example, assist in loading system 16, delivering medical device 10 and/or withdrawing system 16 from a body lumen. In some embodiments, one or more components can include a multi-layer design, including for example one or more layers can be made entirely or partially of polymer. In some embodiments, one or more layers can be made entirely or partially of high-density polyethylene (HDPE). In some embodiments, one or more layers can be made entirely or partially of polytetrafluoroethylene (PTFE).

The foregoing description of the invention has been presented for purposes of illustration and description. It is not intended to be exhaustive or to limit the invention to the precise form disclosed. Other modifications and variations can be possible in light of the above teachings. The embodiments and examples were chosen and described in order to best explain the principles of the invention and its practical application and to thereby enable others skilled in the art to best utilize the invention in various embodiments with modifications as are suited to the particular use contemplated. It is intended that the appended claims be construed to include other alternative embodiments of the invention.

The invention claimed is:

1. A medical device delivery system comprising:
    a handle including an actuator;
    a dilator attached to the handle via an inner shaft;
    a capsule disposed adjacent to the dilator, wherein the capsule is configured to house a medical device for use with the medical device delivery system between the capsule and the inner shaft, wherein the capsule is configured to move relative to the dilator via movement of the actuator to release the medical device; and
    a flap that radially protrudes from the dilator, wherein the flap includes a first end coupled to the dilator and a second free end disposed radially spaced from the dilator, wherein the flap is disposed radially outward from the dilator in a first configuration and is configured to bend in a first direction against a body lumen to cover at least an edge of the capsule located on one side of the flap when the dilator is tracked through the body lumen and is configured to bend in a second direction, opposite the first direction, to cover a portion of the dilator disposed on an opposite side of the flap.

2. The system of claim 1, wherein the flap is configured to bend in the first direction when the dilator is tracked through the body lumen in the second direction opposite the first direction.

3. The system of claim 1, wherein the flap protrudes from the dilator at an angle of approximately 90 degrees.

4. The system of claim 1, wherein the system includes two flaps that radially protrude from the dilator.

5. The system of claim 1, wherein the dilator includes a recess, wherein the flap is disposed in the recess when the flap is bent to cover at least a portion of the delivery system.

6. The system of claim 1, wherein the flap comprises four flaps.

7. The system of claim 1, wherein the flap comprises a polymer film.

8. The system of claim 1, further comprising:
    a sheath extending proximally from the capsule; and
    an introducer disposed over the sheath.

9. A medical device delivery system comprising:
    a dilator; and
    at least two flaps that radially protrude from the dilator, wherein the two flaps are formed from a single piece of flap material that passes through the dilator and are configured to bend against a body lumen to cover at least a portion of the delivery system when the dilator is tracked through the body lumen.

10. The system of claim 9, wherein the single piece of flap material is sandwiched between a first portion of the dilator and a second portion of the dilator.

11. The system of claim 10, wherein the first portion and the second portion of the dilator are sandwiched around the single piece of flap material and bonded together.

12. The system of claim 9, wherein the dilator includes a guidewire lumen disposed therethrough, and wherein the single piece of flap material includes an opening disposed therethrough, wherein the opening of the single piece of flap material is aligned with the guidewire lumen.

13. The system of claim 12, wherein the single piece of flap material is sandwiched between a first portion of the dilator and a second portion of the dilator, wherein the first portion of the dilator includes an extension that extends toward the second portion of the dilator, wherein the single piece of flap material includes a second opening, and wherein the extension extends through the second opening.

14. The system of claim 9, wherein each of the two flaps protrude from the dilator at an angle of approximately 90 degrees relative to a longitudinal axis of the dilator.

15. The system of claim 9, wherein the single piece of flap material comprises a polymer film.

16. A medical device delivery system comprising:
 a dilator; and
 four flaps that radially protrude from the dilator, wherein the four flaps are formed from a single piece of flap material that passes through the dilator and are configured to bend against a body lumen to cover at least a portion of the delivery system when the dilator is tracked through the body lumen.

17. The system of claim 16, wherein the single piece of material is X-shaped.

18. The system of claim 16, wherein each of the four flaps protrudes from the dilator at an angle of approximately 90 degrees relative to a longitudinal axis of the dilator.

19. The system of claim 16, wherein the single piece of flap material is sandwiched between a first portion of the dilator and a second portion of the dilator.

20. The system of claim 16, wherein the dilator includes a guidewire lumen disposed therethrough, and wherein the single piece of flap material includes an opening disposed therethrough, wherein the opening of the single piece of flap material is aligned with the guidewire lumen.

21. The system of claim 16, wherein the single piece of flap material comprises a polymer film.

* * * * *